United States Patent [19]

Höchstetter

[11] Patent Number: 5,164,496

[45] Date of Patent: Nov. 17, 1992

[54] TRICYCLE PYRAZINE DYES

[75] Inventor: Hans Höchstetter, Duesseldorf, Fed. Rep. of Germany

[73] Assignee: Bayer Aktiengesellschaft, Leverkusen, Fed. Rep. of Germany

[21] Appl. No.: 735,711

[22] Filed: Jul. 26, 1991

Related U.S. Application Data

[63] Continuation of Ser. No. 523,087, May 14, 1990, abandoned.

[30] Foreign Application Priority Data

Jun. 3, 1989 [DE] Fed. Rep. of Germany ....... 3918178

[51] Int. Cl.⁵ ............... C07D 491/153; C07D 487/14; C07D 241/02; C07D 495/14
[52] U.S. Cl. .................................. 540/544; 540/553; 540/575; 540/599; 544/115; 544/180; 544/182; 544/345; 544/212; 544/219; 544/235; 544/237; 544/238; 544/245; 544/247; 544/284; 544/316; 544/317; 544/319; 544/320; 544/321; 544/322; 544/328; 544/331; 544/333; 544/342; 544/343; 544/383
[58] Field of Search ............... 544/345, 115, 180, 182, 544/212, 219, 316, 317, 319, 320, 321, 322, 328, 331, 333, 235, 237, 238, 284; 540/544, 553, 575, 599

[56] References Cited

U.S. PATENT DOCUMENTS 3,407,203 10/1968 Buijle ................................. 544/383
3,763,091 10/1973 Crescenzi et al. ................... 544/383

FOREIGN PATENT DOCUMENTS 2116262 10/1971 Fed. Rep. of Germany .

OTHER PUBLICATIONS

Shin Chemical Abstracts, vol. 80 47943b 1974.
Tetrahedron, vol. 30 1974, pp. 667–673; Gal Lina et al.; Condensation of 1,4-diacetylpiperazine-2,5-Dione with Aldehydes.

Primary Examiner—Mark L. Berch
Attorney, Agent, or Firm—Sprung Horn Kramer & Woods

[57] ABSTRACT

Compounds of the formula

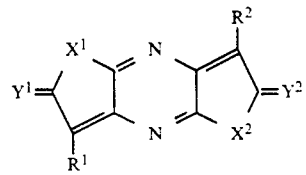

in which $R^1$, $R^2$, $X^1$, $X^2$, $Y^1$ and $Y^2$ have the following meanings $R^1$ and $R^2$ designate optionally substituted aryl, or an optionally substituted heterocyclic radical which contain 1 or 2 five-, six- or seven-membered rings at least one of which contains 1, 2 or 3 hetero atoms from the series comprising O, N and S which has a C=C in conjugation with the C=C bond in the five-membered ring of III, $X^1$, $X^2$, $Y^1$ and $Y^2$ designate O, S, $NR^5$, or $X^1$ and $Y^1$ or $X^2$ and $Y^2$ in each case form parts of a fused-on heterocyclic five-membered or six-membered ring, processes for their preparation and their use as dyestuffs and pigments.

3 Claims, No Drawings

TRICYCLE PYRAZINE DYES

This application is a continuation of application Ser. No. 523,087, filed May 14, 1990, now abandoned.

The invention relates to heterocyclic compounds which correspond, in one of their tautomeric or configuration isomer forms, to the formula

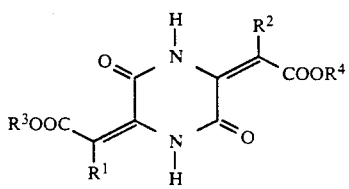

and compounds of the formulae

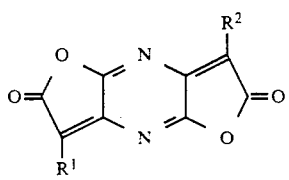

and

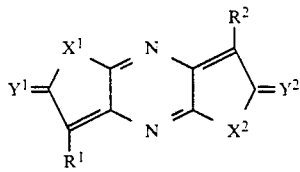

with the following meanings of substituents:

$R^1$, $R^2$ = optionally substituted aryl, or an optionally substituted heterocyclic radical which has a C=X bond (X=C or hetero atom) in conjugation with the exocyclic double bond of I or with the C=C bond in the five-membered rings in II or III, $R^3$, $R^4$ = H, optionally substituted alkyl, optionally substituted aryl, optionally substituted cycloalkyl or optionally substituted aralkyl, $X^2$, $X^2$, $Y^1$, $Y^2$ = O, S, NH, or $NR^5$. $X^1$ and $Y^1$ or $X^2$ and $Y^2$ can also in each case form parts of a fused-on heterocyclic five-membered or six-membered ring, which then preferably contains 2 N atoms.

$R^5$ = hydrogen, optionally substituted alkyl, optionally substituted aryl, optionally substituted cycloalkyl, optionall substituted aralkyl or an optionally substituted heterocyclic radical.

In the formulae I to III, $R^1$ is preferably identical to $R^2$. The invention furthermore relates to processes for the preparation of the compounds I to III and their use.

Alkyl preferably represents $C_1$–$C_{18}$-alkyl, in particular $C_1$–$C_4$-alkyl. Cycloalkyl preferably represents $C_3$–$C_7$-cycloalkyl, in particular cyclohexyl or cyclopentyl. Possible substituents of the alkyl and cycloalkyl radicals are, for example: halogen, such as Cl, Br and F, CN, OCOR , $OR^7$, $COOR^{10}$, $SR^7$, $CONR^8R^9$ and $OCONR^8R^9$, wherein $R^7$ to $R^{10}$ have the meanings given below.

Aralkyl represents, in particular, phenyl- and naphthyl-$C_1$–$C_4$-alkyl, wherein the aryl radicals substituted, for example as described below for aryl.

Aryl preferably represents those carbocyclicaromatic radicals which contain 1, 2, 3 or 4, in particular 1 or 2 rings, such as phenyl, diphenylyl and naphthyl.

Preferred heterocyclic radicals are those heterocyclic (aromatic) radicals which contain 1, 2, 3 or 4, in particular 1 or 2 five-, six- or seven-membered rings, at least one of which contains 1, 2 or 3, preferably 1 or 2 hetero atoms from the series comprising O, N and S. Heterocyclic radicals which may be mentioned as examples are:

pyridyl, pyrimidyl, pyrazinyl, triazinyl, furoyl, pyrrolyl, thiophenyl, quinolyl, cumarinyl, benzofuranyl, benzimidazolyl, benzoxazolyl, dibenzofuranyl, benzothiophenyl, dibenzothiophenyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazindionyl, phthalamidyl, chromonyl, naphtholactamyl, quinolonyl, orthosulphobenzimidyl, maleimidyl, naphtharidinyl, benzimidazolonyl, benzoxazolonyl, benzothiazolonyl, benzothiazothionyl, quinazolonyl, quinoxalonyl, phthalazonyl, dioxopyrimidinyl, pyridonyl, isoquinolcnyl, isoquinolinyl, isothiazolyl, benzisoxazolyl, benzisothiazolyl, indazolonyl, acridinyl, acridonyl, quinazolinedionyl, quinoxalinedionyl, benzoxazinedionyl, benzoxazinonyl and naphthalimidyl.

The aryl and heterocyclic radicals can be substituted, for example, by halogen, such as chlorine, bromine and fluorine, —CN, $R^6$, $OR^7$, $SR^7$, $NR^8R^9$, $COOR^{10}$, $COR^{10}$, $NR^8COR^{10}$, $NR^8COOR^{10}$, $NR^8CONR^8R^9$, $NHSO_2R^{10}$, $SO_2R^{10}$, $SO_2OR^{10}$, $CONR^8R^9$, $SO_2NR^8R^9$, $N=N-R^{11}$, $OCOR^{10}$ and $OCONR^8R^9$.

$R^6$ designates optionally substituted alkyl, preferably $C_1$–$C_{18}$-alkyl, in particular $C_1$–$C_4$-alkyl, or optionally substituted cycloalkyl, preferably $C_3$–$C_7$-cycloalkyl, in particular cyclohexyl or cyclopentyl.

Possible substituents of the alkyl and cycloalkyl radicals $R^6$ are, for example: halogen, such as Cl, Br and F, CN, $OCOR^{10}$, $OR^7$, $COOR^{10}$, $SR^7$, $CONR^8R^9$ and $OCONR^8R^9$.

$R^7$, $R^8$ and $R^9$ designate hydrogen, optionally substituted alkyl, in particular $C_1$–$C_{18}$ -alkyl, preferably $C_1$–$C_4$-alkyl, optionally substituted cycloalkyl, in particular cyclohexyl or cyclopentyl, optionally substituted aralkyl, in particular phenyl- or naphthyl-$C_1$–$C_4$-alkyl, optionally substituted aryl, in particular phenyl or naphthyl, or an optionally substituted heterocyclic radical, in particular the radical of a 5- or 6-membered heterocyclic ring containing 1, 2 or 3 hetero atoms from the series comprising O, N and S, onto which a benzene ring may be fused.

The alkyl and cycloalkyl radicals $R^7$, $R^8$ and $R^9$ can be substituted, for example, by Cl, Br, F, CN, mono-$C_1$–$C_4$-alkylamino, di-$C_1$–$C_4$-alkylamino, phenyl or naphthyl, which can be substituted by Cl, Br, F, $C_1$–$C_6$-alkyl or $C_1$–$C_6$-alkoxy, or by heterocyclic radicals of a 5- or 6-membered heterocyclic ring system containing 1 or 2 hetero atoms from the series comprising O, N and S, onto which a benzene ring may be fused.

$R^8$ and $R^9$ together, including the N atom, can also form a 5- or 6-membered heterocyclic ring, for example a morpholine, piperidine or phthalimide ring. The aryl and aralkyl radicals $R^8$ and $R^9$ can be substituted, for example, by Cl, Br, F or $C_1$–$C_{18}$-alkyl, preferably $C_1$–$C_4$-alkyl, alkyl, or by $C_1$–$C_{18}$-alkoxy, preferably $C_1$$C_4$-alkoxy.

$R^{10}$ designates hydrogen, optionally substituted alkyl, in particular $C_1$–$C_{18}$-alkyl, preferably $C_1$–$C_4$-alkyl, optionally substituted cycloalkyl, in particular cyclopentyl or cyclohexyl, optionally substituted aralkyl, in particular phenyl- or naphthyl-$C_1$-$C_4$-alkyl, preferably benzyl, or optionally substituted aryl, in particular phenyl or naphthyl.

The radicals mentioned for R can be substituted in the same way as the corresponding radicals $R^8$ and $R^9$.

$R^{11}$ designates the radical of a coupling component, preferably of a coupling component from the benzene, naphthalene, acetoacetate arylide, pyrazole or pyridone series, or a phenyl radical which is optionally substituted by Cl, Br, F, $C_1$-$C_{18}$-alkyl, preferably $C_1$-$C_4$-alkyl, or $C_1$-$C_{18}$-alkoxy, preferably $C_1$-$C_4$-alkoxy.

The radicals $R^3$ and $R^4$ in the formula I can assume the meaning of $R^8$ and $R^9$.

To prepare compounds of the formula I, glycine anhydride derivatives, which are known from the literature or can be prepared by processes analogous to those known from the literature, of the formula

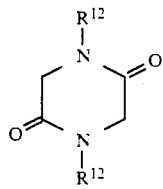    IV are reacted with compounds of the formulae

    V and

    VI

The radical $R^{12}$ can denote hydrogen or $COR^5$, $R^1$ to $R^5$ having the abovementioned meanings.

The reaction is preferably carried out in the presence of a basic catalyst. Suitable preferred catalysts are aliphatic amines, in particular tertiary aliphatic amines, such as, for example, triethylamine.

Equimolar amounts of the catalyst and substrate V/VI are preferably employed.

The reaction is preferably carried out at a temperature of 30 to 100° C., particularly preferably 50 to 70° C.

The reaction can be carried out without a solvent. However, it can also be carried out in solvents. Examples of suitable solvents are alcohols or dipolar aprotic solvents, such as acetonitrile, dimethyl sulphoxide and in particular dimethylformamide.

All three possible configuration isomers I a, I b and I c

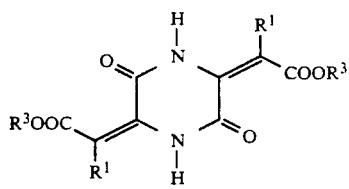    Ia

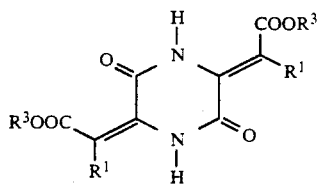    Ib

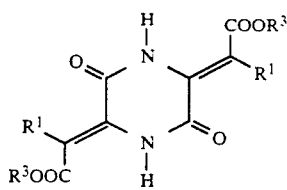    Ic are usually formed in the reaction according to the invention. It is possible for the three isomers to be separated by chromatography and characterized individually.

Compounds of the formula II can be prepared by heating piperazine derivatives of the formula I in high-boiling solvents in the presence of a suitable catalyst or in dehydrating agents, such as acetic anhydride or phosphorus oxychloride. Examples of suitable solvents are o-dichlorobenzene or high-boiling aromatic hydrocarbons or ethers, and a possible catalyst is p-toluenesulphonic acid or sulphuric acid. The reaction is carried out at temperatures between 120 and 240° C., preferably at 160 to 180° C.

Compounds of the formula III are prepared by reacting compounds of the formula I or II with virtually any desired primary amines in high-boiling solvents, if appropriate in the presence of a suitable catalyst, water or water and alcohol being split off. The compounds of the formula II exhibit a similar reactivity here to aromatic carboxylic acid anhydrides, for example perylenetetracarboxylic dianhydride.

As already mentioned, virtually any primary amine can be employed, and even highly sterically hindered amines, such as 2,6-diethyl-4-methylaniline, or amines of very low basicity, such as aromatic amines containing nitro groups or cyano groups, react to give the reaction products of the formula III. If appropriate, low-boiling aliphatic amines can be reacted in an autoclave.

Compounds of the formula VII where $R^5$ =hydrogen are prepared by heating compounds of the formula I in formamide.

Possible high-boiling solvents for carrying out the reaction according to the invention are, for example: (chlorinated) aromatic hydrocarbons, such as xylene, chlorobenzene, dichlorobenzenes, trichlorobenzenes, naphthalene or chloronaphthalene. Quinoline is particularly suitable. However, water (in an autoclave) can also be employed, or the amine in question can itself function as the solvent as long as it has a sufficiently high boiling point. It may prove advantageous to remove the resulting water of reaction azeotropically.

The reaction preferably proceeds at temperatures of 130 to 250° C., particularly preferably between 180 and 210° C.

Suitable catalysts are mineral acids, carboxylic acids, sulphonic acids or suitable metal salts, such as, for example, zinc acetate or zinc chloride.

Compounds of the formula III where $X^1$ and $X^2$ =S are prepared by replacing the O atoms in II by S, for example by sulphurization with Lawesson's reagent or with anhydrous $H_2S$.

To prepare compounds of the formula III in which $X^1$ and $Y^1$ or $X^2$ and $Y^2$ form parts of a fused-on heterocyclic five- or six-membered ring containing 2 N atoms, compounds II are reacted with primary aromatic diamines, for example 1,8-diaminonaphthalene or o-phenylenediamines. A representative of this type of compound is shown by the following formula:

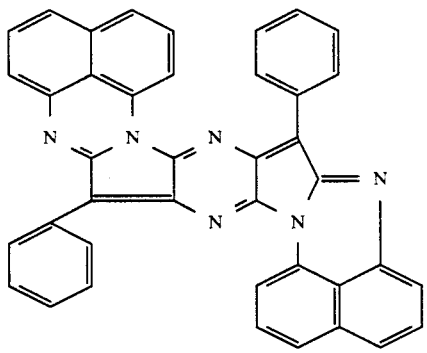

Preferred compounds of the formula III are those which correspond to the formula

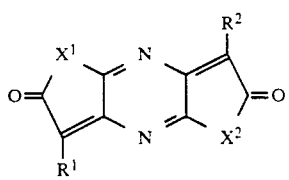     VI and in particular to the formula

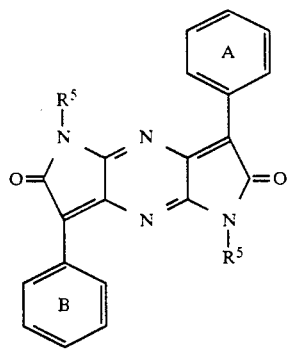     VII wherein the rings designated A and B can be substituted, for example, by halogen, such as Cl, Br or F, —NHCOR$^8$ and/or —NR$^8$R$^9$, wherein R$^8$ and R$^9$ have the abovementioned meanings.

The compounds of the formula I are used in particular as intermediate products for the preparation of useful dyestuffs and pigments, in particular for the preparation of the compounds II.

Compounds of the formula II can be used as dyestuffs or as intermediate products for the preparation of dyestuffs or pigments, in particular III. Thus, the compounds of the formula II can be used as soluble dyestuffs for colouring plastics (polystyrene) or, if appropriate, also after prior introduction of lipophilic radicals, as disperse dyestuffs.

Compounds of the formula III can be used in particular as dyestuffs or pigments, in particular for pigmenting high molecular weight organic material.

The compounds of the formula III are obtained in a form suitable for pigment use or can be converted into the suitable form by after-treatment processes which are known per se, for example by dissolving or swelling in strong inorganic acids, such as sulphuric acid, and discharging onto ice. Fine division can also be achieved by grinding with or without grinding auxiliaries, such as inorganic salts or sand, if appropriate in the presence of solvents, such as toluene, xylene, dichlorobenzene or N-methylpyrrolidone. The tinctorial strength and transparency of the pigment can be influenced by varying the after-treatment.

Because of their fastness to light and migration, the compounds of the formula III are suitable for the most diverse pigment applications. Thus, they can be used for the preparation of systems which have a very fast pigmentation as a mixture with other substances, formulations, paints, printing agents, coloured paper and coloured macromolecular substances. A mixture with other substances may be understood as, for example, that with inorganic white pigments, such as titanium dioxide (rutile) or with cement. Formulations are, for example, flush pastes with organic liquids or pastes and fine pastes with water, dispersing agents and if appropriate preservatives. The designation paint represents, for example, lacquers which dry by physical or oxidative means, stoving lacquers, reactive lacquers, two-component lacquers, emulsion paints for weatherproof coatings and distempers.

Printing inks are to be understood as those for printing paper, textiles and sheet metal. The macromolecular substances can be of natural origin, such as rubber, obtained by chemical modification, such as acetylcellulose, cellulose butyrate or viscose, or produced synthetically, such as polymers, polyaddition products and polycondensates. Substances which may be mentioned are plastic compositions, such as polyvinyl chloride, polyvinyl acetate, polyvinyl propionate, polyolefines, for example polyethylene, or polyamides, high molecular weight polyamides, polymers and copolymers of acrylic ester, methacrylic esters, acrylonitrile, acrylamide, butadiene and styrene, and polyurethanes and polycarbonates. The substances pigmented with the products claimed can also be in any desired form.

The pigments of the formula III are furthermore excellently water-fast, oil-fast, acid-fast, lime-fast, alkali-fast, solvent-fast, overlacquering-fast, overspraying-fast, sublimation-fast, heat-stable and vulcanization-stable, of very high tinctorial strength and easily distributed in plastic compositions.

EXAMPLE 1

45.6 g of bisacetylated glycine anhydride (IV, R$^{12}$=COCH$_3$), 90.6 g of methyl phenylglyoxylate and 89.8 g of triethylamine are stirred at 55 to 60° C. for 8.5 hours. The triethylamine is then largely stripped off in vacuo and the oily-crystalline residue is stirred with 50 ml of methanol for 12 hours. The mixture is then cooled to 0° C. and subsequently stirred after 2 hours and the product is filtered off with suction and washed with ice-cold methanol. 78.2 g of the isomer mixture of

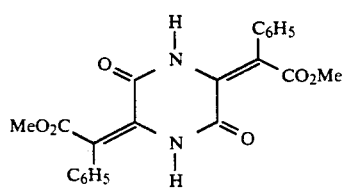     Id obtained as yellow-white crystalline substance.

NMR (DMSO):

δ=3.64 (s, 6H, OCH₃), 7.15–7.35 (m, 10H), 11.56 ppm (bs, 2H, NH): 1st isomer

=3.68 (s, 3H, OCH₃), 3.73 (s, 3H, OCH₃), 7.15–7.38 (m, 10H, aromatic H), 11.40 (bs, 1H, NH), 11.56 (bs, 1H, NH): 2nd isomer δ=3.66 (s, 6H, OCH₃), 7.38–7.52 (m, 10H, aromatic H), 10.20 ppm (bs, 2H, NH): 3rd isomer Compounds I according to the invention where $R^3$ and $R^4$ = H are prepared by dissolving compounds of the formula I where $R^3$ and $R^4 \neq$ H in 96 per cent strength sulphuric acid at temperatures of 40 to 80° C., preferably 50 to 60° C., and then precipitating the product again by dilution with water, while cooling. These carboxylic acid derivatives are also useful intermediate products for the preparation of organic dyestuffs and pigments. The reaction can also be carried out completely analogously to Example 1 using methyl 4-chlorophenylglyoxylate, which leads to an isomer mixture.

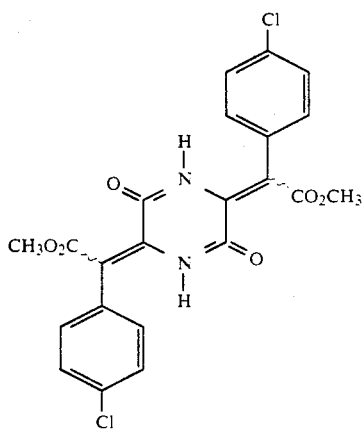

Ie

EXAMPLE 2

10 g of the isomer mixture I d obtained in Example 1 are boiled under reflux in 50 ml of o-dichlorobenzene in the presence of 0.1 g of p-toluenesulphonic acid for 8 hours. After cooling, the product is filtered off with suction and washed with methanol. 6 g of a black-violet crystalline powder are obtained.

UV (DMF): $\lambda_{max}$ =488 nm (41,800)

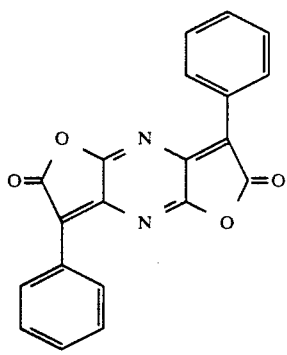

Incorporation of this substance into polystyrene gives an orange-red coloration.

EXAMPLE 3

6.5 g of the isomer mixture I d prepared in Example 1 are stirred in 20 ml of formamide at 150° C. for 4 hours. After the mixture has been stirred with 20 ml of methanol, 4 g of the compound

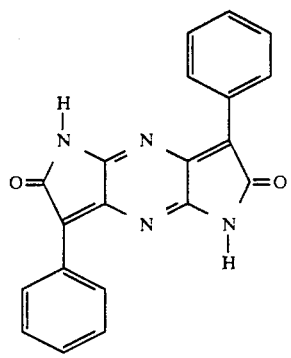

$\lambda_{max}$ = 471 nm (25,600)

are isolated, the compound giving a red-orange coloration when incorporated into polystyrene.

EXAMPLE 4

10 g of the isomer mixture I d prepared according to Example 1 are boiled under reflux together with 6.3 g of 4-chloroaniline and 100 mg of p-toluenesulphonic acid in 50 ml of o-dichlorobenzene for 12 hours. After the product has been filtered off with suction at room temperature, 10 g of the compound

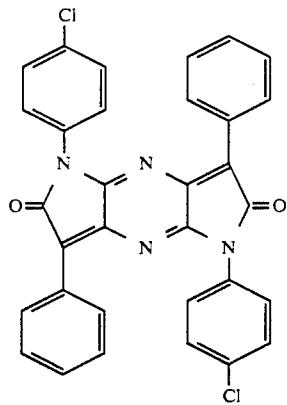

$\lambda_{max}$ = 484 nm are isolated, the compound being a bluish-tinged red pigment.

EXAMPLE 5

10.3 g of the isomer mixture I d prepared according to Example 1 are stirred together with 13.0 g of 4-aminoazopbenzene and 0.1 g of zinc acetate in 100 ml of quinoline at 190 to 195° C. for 2 hours. After cooling to 65° C., the mixture is stirred with 100 ml of ethanol and the product is filtered off with suction. 12 g of a brown-red pigment of the formula

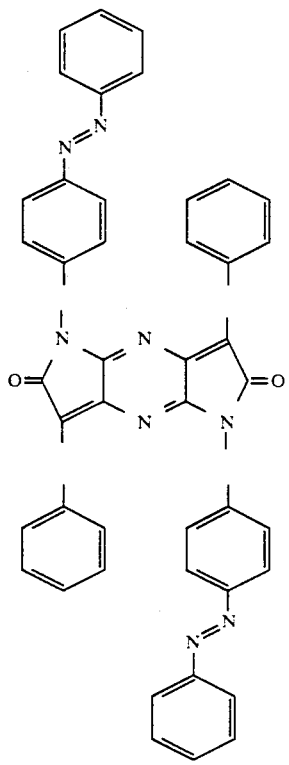

are isolated.

Instead of the isomer mixture I d, it is also possible to employ the isomer mixture I e (4-chlorophenyl derivative) in each case.

The dyestuffs and pigments listed in the following Table 1 are obtained by procedures analogous to those of Example 3-5.

TABLE 1

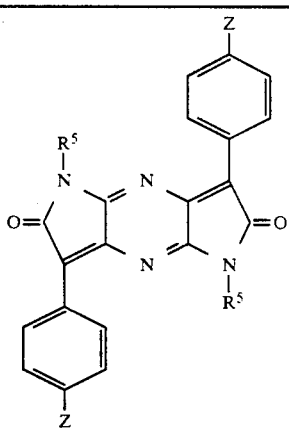

| Example No. | Z | R⁵ | Comments |
|---|---|---|---|
| 6 | H | n-butyl | brown-red soluble dyestuff |
| 7 | Cl | n-butyl | brown-red soluble dyestuff |
| 8 | H | CH₃ | brown-red soluble dyestuff |

TABLE 1-continued

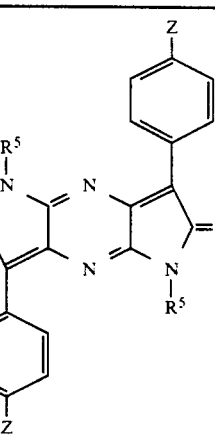

| Example No. | Z | R⁵ | Comments |
|---|---|---|---|
| 9 | Cl | CH₃ | brown-red soluble dyestuff |
| 10 | H | hexadecyl | red dyestuff |
| 11 | H | —CH₂—CH₂—OH | red dyestuff |
| 12 | H | 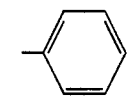 | red dyestuff |
| 13 | Cl | 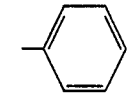 | red pigment |
| 14 | H | 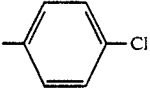 | red-violet pigment |
| 15 | Cl | 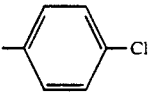 | red-violet pigment |
| 16 | H | 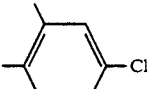 | orange-red pigment |
| 17 | Cl | 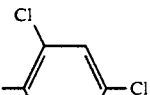 | orange-red pigment |
| 18 | H | 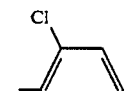 | brown-red pigment |

TABLE 1-continued

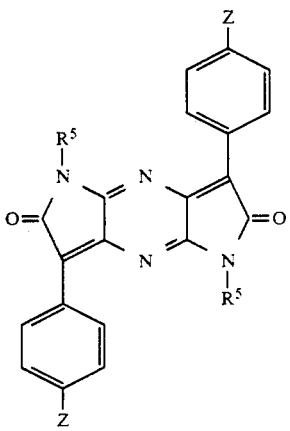

| Example No. | Z | R⁵ | Comments |
|---|---|---|---|
| 19 | H | 3,4-dichlorophenyl | brown-red pigment |
| 20 | Cl | 3,4-dichlorophenyl | brown-red pigment |
| 21 | H | 4-(N,N-diethylamino)phenyl | red dyestuff |
| 22 | Cl | 4-(N,N-diethylamino)phenyl | red dyestuff |
| 23 | H | 4-carbamoylphenyl | red-violet pigment |
| 24 | Cl | 4-carbamoylphenyl | red-violet pigment |
| 25 | H | 2-pyridyl | red dyestuff |
| 26 | Cl | 2-pyridyl | red dyestuff |

TABLE 1-continued

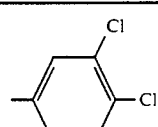

| Example No. | Z | R⁵ | Comments |
|---|---|---|---|
| 27 | H | 2-(acetylamino)-phenyl (NHC(O) substituted) | brown-red pigment |
| 28 | Cl | 2-(acetylamino)-phenyl (NHC(O) substituted) | brown-red pigment |
| 29 | H | benzimidazol-2-yl | brown-red pigment |
| 30 | Cl | benzimidazol-2-yl | brown-red pigment |
| 31 | H | 2-cyano-4-chlorophenyl | red pigment |
| 32 | Cl | 2-cyano-4-chlorophenyl | red pigment |

TABLE 1-continued

[Structure for examples 33-39: pyrrolo-pyrazine-dione with Z-phenyl groups and R⁵ on nitrogens]

| Example No. | Z | R⁵ | Comments |
|---|---|---|---|
| 33 | H | 2,5-dimethylphenyl (CH₃, CH₃) | red dyestuff |
| 34 | Cl | 2,5-dimethylphenyl (CH₃, CH₃) | red dyestuff |
| 35 | H | 4-tert-butylphenyl —C(CH₃)₃ | red dyestuff |
| 36 | Cl | 4-tert-butylphenyl —C(CH₃)₃ | red dyestuff |
| 37 | H | 3-Cl-4-CONH₂-phenyl | brown-red pigment |
| 38 | Cl | 3-Cl-4-CONH₂-phenyl | brown-red pigment |
| 39 | H | 1H-1,2,4-triazol-3-yl (with N—N, NH) | red-orange pigment |

TABLE 1-continued

[Isomeric structure for examples 40-47]

| Example No. | Z | R⁵ | Comments |
|---|---|---|---|
| 40 | Cl | 1H-1,2,4-triazol-3-yl | red-orange pigment |
| 41 | H | 2,6-diethyl-4-methylphenyl (C₂H₅, CH₃, C₂H₅) | red dyestuff |
| 42 | Cl | 2,6-diethyl-4-methylphenyl (C₂H₅, CH₃, C₂H₅) | red dyestuff |
| 43 | H | 3-NHCOCH₃-phenyl | brown-red pigment |
| 44 | Cl | 3-NHCOCH₃-phenyl | brown-red pigment |
| 45 | H | 4-NHCOCH₃-phenyl | brown-red pigment |
| 46 | Cl | 4-NHCOCH₃-phenyl | brown-red pigment |
| 47 | H | 4-NH₂-phenyl | red dyestuff |

TABLE 1-continued

| Example No. | Z | R⁵ | Comments |
|---|---|---|---|
| 48 | Cl | 4-aminophenyl (p-H₂N-C₆H₄-) | red dyestuff |
| 49 | H | 1-anthraquinonyl | red pigment |
| 50 | Cl | 1-anthraquinonyl | red pigment |
| 51 | H | 2-CF₃-4-Cl-phenyl | orange-red dyestuff |
| 52 | Cl | 2-CF₃-4-Cl-phenyl | orange-red dyestuff |
| 53 | H | 2-chlorophenyl | orange dyestuff |
| 54 | Cl | 2-chlorophenyl | orange dyestuff |
| 55 | H | 2-benzothiazolyl | black-brown pigment |
| 56 | Cl | 2-benzothiazolyl | black-brown pigment |
| 57 | H | 2-(4-methylphenyl)-6-methylbenzothiazolyl | brown pigment |
| 58 | Cl | 2-(4-methylphenyl)-6-methylbenzothiazolyl | brown pigment |
| 59 | H | 2-hydroxyphenyl | brown-red dyestuff |
| 60 | Cl | 2-hydroxyphenyl | brown-red dyestuff |
| 61 | H | —CONH-phenyl | brown-red dyestuff |
| 62 | Cl | —CONH-phenyl | brown-red dyestuff |
| 63 | H | 4-bromophenyl | red-brown pigment |
| 64 | Cl | 4-bromophenyl | red-brown pigment |

TABLE 1-continued

| Example No. | Z | R⁵ | Comments |
|---|---|---|---|
| 65 | H | 4-methylphenyl-N=N-N(phenyl) hydrazone | brown pigment |
| 66 | Cl | 4-methylphenyl-N=N-N(phenyl) hydrazone | brown pigment |
| 67 | H | 3-methyl-5-carboxy-1H-1,2,4-triazole | red pigment |
| 68 | Cl | 3-methyl-5-carboxy-1H-1,2,4-triazole | red pigment |
| 69 | H | 2-methyl-4-phenyl-1,3-thiazole | red pigment |
| 70 | Cl | 2-methyl-4-phenyl-1,3-thiazole | red pigment |
| 71 | H | 1-phenyl-3-methyl-5-amino-1,2,4-triazole (amidrazone) | red pigment |
| 72 | Cl | 1-phenyl-3-methyl-5-amino-1,2,4-triazole (amidrazone) | red pigment |
| 73 | H | 2-methylthiazole | red dyestuff |
| 74 | Cl | 2-methylthiazole | red dyestuff |
| 75 | H | 4-sulfamoylphenyl (—C₆H₄—SO₂NH₂) | red dyestuff |

TABLE 1-continued

[chemical structure diagram]

| Example No. | Z | R⁵ | Comments |
|---|---|---|---|
| 76 | Cl | —⟨phenyl⟩—SO₂NH₂ | red dyestuff |

EXAMPLE 77 (USE EXAMPLE)

4 g of finely ground pigment according to Example 5 are dispersed in 92 g of a stoving lacquer of the following composition:
33 % of alkyd resin
15 % of melamine resin
5 % of glycol monomethyl ether
34 % of xylene
13 % of butanol Possible alkyd resins are products based on synthetic and vegetable fatty acids, such as coconut oil, castor oil, dehydrated castor oil, linseed oil and the like. Urea resins can be used instead of melamine resins. After the dispersion has been carried out, the pigmented lacquer is applied to films of paper, glass, plastic or metal and stoved at 130° C. for 30 minutes. The lacquerings have very good resistance to light and weathering and a good fastness to overlacquering.

The stoving lacquer prepared according to Example 77 is brushed onto white paper and stoved at 130° C.

EXAMPLE 78 (USE EXAMPLE)

0.2 g of pigment according to Example 5 is mixed with 100 g of granules of polyethylene, polypropylene or polystyrene. The mixture can either be injection-moulded at 220 to 280° C. directly in an injection-moulding machine, or processed to coloured bars in an extruder or to coloured hides on a mixing roll mill. The bars or hides are granulated, if appropriate, and injection-moulded in an injection-moulding machine.

The red mouldings have very good fastness to light and migration. Synthetic polyamides of caprolactam or adipic acid and hexamethylenediamine or the condensates of terephthalic acid and ehtylene glycol can be coloured in a similar manner at 280 to 300° C., if appropriate under a nitrogen atmosphere.

I claim:
1. Compounds of the formula

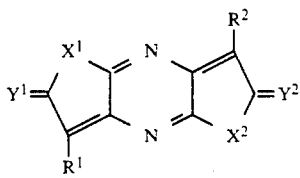

III in which
$R^1$ and $R^2$ designate optionally substituted aryl, or an optionally substituted heterocyclic aromatic radical which heterocyclic aromatic radical contains 1 or 2 five-, or six-membered rings at least one of which contains 1, 2 or 3 hetero atoms from the series comprising O, N and S which has a C=S in conjugation with the C=C bond in the five-membered ring of III, $X^1$ and $X^2$ designate $NR^5$, $Y^1$ and $Y^2$ designate O, S, or $NR^5$   $R^5$ represents hydrogen, optionally substituted alkyl, optionally substituted aryl, optionally substituted cycloalkyl or a heterocyclic radical having 1 or 2 five- , six - or seven-membered rings, at least one of which contains 1 or 2 heteroatoms from the group consisting of O, N and S, wherein in each of the above, where called for, the aryl and heterocyclic radicals can be substituted by chlorine, bromine, and fluorine, —CN, $R^6$, $OR^7$, $SR^7$, $NR^8R^9$, $COOR^{10}$, $COR^{10}$, $NR^8COR^{10}$, $NR^8COOR^{10}$, $NR^8CONR^8R^9$, $NHSO_2R^{10}$, $SO_2R^{10}$, $SO_2OR^{10}$, $CONR^9R^9$, $SO_2NR^8R^9$, $N=N—R^{11}$, $OCOR^{10}$ and $OCONR^8R^9$, wherein, $R^6$ designates optionally substituted alkyl, or optionally substituted cycloalkyl, substituents of the alkyl and cycloalkyl radicals are, Cl, Br and F, CN, $OCOR^{10}$, $OR^7$, $COOR^{10}$, $SR^7$, $CONR^8R^9$ and $OCONR^6R^9$, wherein $R^7$ and $R^{10}$ have the following meanings:

$R^7$, $R^8$ and $R^9$ designate hydrogen, optionally substituted $C_1$-$C_{18}$-alkyl, optionally substituted cycloalkyl, aralkyl, aryl, or the radical of a 5- or 6-membered heterocyclic ring containing 1, 2, or 3 hetero atoms from the series comprising O, N and S, onto which a benzene ring may be fused;

$R^8$ and $R^9$ together, including the N atom, can also form a ring selected from the group consisting of morpholine, piperidine or phthalimide rings;

wherein $R^7$, $R^8$ and $R^9$ are alkyl or cycloalkyl radicals they can be substituted by Cl, Br, F, CN, mono-$C_1$-$C_4$-alkylamino, di-$C_1$-$C_4$-alkylamino, phenyl or naphthyl, which can be substituted by Cl, Br, F, $C_1$-$C_6$-alkyl or $C_1$-$C_6$-alkoxy, or by heterocyclic radicals of a 5- or 6-membered heterocyclic ring system containing 1 to 2 hetero atoms from the series comprising O, N and S, onto which a benzene ring may be fused;

when $R^8$ and $R^9$ are aryl or aralkyl radicals they can be substituted by Cl, Br, F or $C_1$-$C_{18}$-alkyl or by $C_1$-$C_{18}$-alkoxy;

$R^{10}$ designates hydrogen, optionally substituted $C_1$-$C_{18}$-alkyl, optionally substituted cycloalkyl, optionally substituted aralkyl, or optionally substituted aryl, wherein the radicals can be substituted in the same manner given above for $R^8$ and $R^9$.

$R^{11}$ designates a benzene, naphthalene, acetoacetate arylide, pyrazole or pyridone radical, or a phenyl radical which may be substituted by Cl, Br, F, C$_1$-C$_{18}$-alkyl.

2. Compounds according to claim 1, of the formula

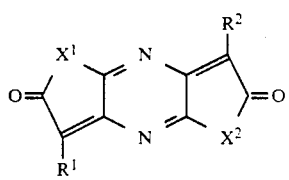

VI

3. Compounds according to claim 1, of the formula

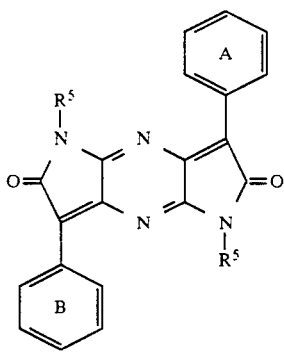

VII wherein the rings designated A and B can be substituted, by Cl, Br or F, —NHCOR$^{10}$ and —NR$^8$R$^9$ in which R$^8$ and R$^9$ designate H, optionally substituted alkyl, optionally substituted cycloalkyl, optionally substituted aralkyl, optionally substituted aryl or R$^8$ and R$^9$ together, including the N-atom, can form a ring selected from the group consisting of morpholine, piperidine and phthalimide rings.

* * * * *

UNITED STATES PATENT AND TRADEMARK OFFICE
CERTIFICATE OF CORRECTION

PATENT NO. : 5,164,496

DATED : November 17, 1992

INVENTOR(S) : Hans Hochstetter

It is certified that error appears in the above-identified patent and that said Letters Patent is hereby corrected as shown below:

| | |
|---|---|
| Title Page & Col. 1 line 1 | [54] Inventeio: Delete " TRICYCLE " and substitute -- TRICYCLIC -- |
| Col. 20, line 16 | Delete " C = S " and substitute -- C = C -- |
| Col. 20, line 33 | Delete " $CONR^9R^9$ " and substitute -- $CONR^8R^9$ -- |
| Col. 20, line 39 | Delete " $OCONR^6R^9$ " and substitute -- $OCONR^8R^9$ --; After " R " delete " and " and substitute -- to -- |
| Col. 20, line 50 | Delete " wherein " and substitute -- when -- |

Signed and Sealed this

Fifth Day of July, 1994

*Attest:*

BRUCE LEHMAN

*Attesting Officer*      Commissioner of Patents and Trademarks